(12) United States Patent
Blanden et al.

(10) Patent No.: US 11,407,791 B2
(45) Date of Patent: Aug. 9, 2022

(54) COMPOSITIONS, METHODS, AND SYSTEMS FOR ORALLY ADMINISTRABLE AFFINITY-BASED PROTEIN

(71) Applicant: Auctus Biologics, Inc., Lafayette, NY (US)

(72) Inventors: Adam Blanden, Lafayette, NY (US); Aaron Wolfe, Syracuse, NY (US)

(73) Assignee: Auctus Biologics, Inc., Lafayette, NY (US)

( * ) Notice: Subject to any disclaimer, the term of this patent is extended or adjusted under 35 U.S.C. 154(b) by 0 days.

(21) Appl. No.: 17/041,780

(22) PCT Filed: Mar. 25, 2019

(86) PCT No.: PCT/US2019/023845
§ 371 (c)(1),
(2) Date: Sep. 25, 2020

(87) PCT Pub. No.: WO2019/190970
PCT Pub. Date: Oct. 3, 2019

(65) Prior Publication Data
US 2021/0188922 A1  Jun. 24, 2021

Related U.S. Application Data

(60) Provisional application No. 62/648,170, filed on Mar. 26, 2018.

(51) Int. Cl.
*A61K 47/42* (2017.01)
*A61K 47/64* (2017.01)
(Continued)

(52) U.S. Cl.
CPC .......... *C07K 14/195* (2013.01); *A61K 9/0053* (2013.01); *A61K 47/26* (2013.01);
(Continued)

(58) Field of Classification Search
CPC .... A61K 9/0053; A61K 9/0065; A61K 47/42; A61K 47/62; A61K 47/64; C07K 14/195
See application file for complete search history.

(56) References Cited

U.S. PATENT DOCUMENTS

2009/0246167 A1   10/2009   Zion et al.

FOREIGN PATENT DOCUMENTS

WO     2017066441 A1      4/2017
WO     WO-2017066441 A1 *  4/2017  ............. C07K 19/00

OTHER PUBLICATIONS

International Search Report and Written Opinion dated Aug. 7, 2019 in connection with PCT/US2019/023845, 10 pages.
(Continued)

*Primary Examiner* — Jeffrey E. Russel
(74) *Attorney, Agent, or Firm* — Dorsey & Whitney LLP (57) ABSTRACT

Disclosed herein are compositions comprising one or more therapeutic proteins for oral administration. The disclosed proteins, which may be directed to a variety of GI and systemic target antigens, resist denaturation and degradation in the stomach and intestines of a patient. The disclosed proteins may be delivered intact to a target region within the gut, or anywhere in body to target specific molecules, cells, tissues, or organs. In some embodiments, the disclosed proteins may include two or more proteins for targeting two or more target antigens.

19 Claims, 4 Drawing Sheets

Specification includes a Sequence Listing.

(51) Int. Cl.
  *C07K 14/195*    (2006.01)
  *A61K 47/55*     (2017.01)
  *A61K 47/52*     (2017.01)
  *A61K 9/00*      (2006.01)
  *A61K 47/26*     (2006.01)
  *A61K 38/00*     (2006.01)

(52) U.S. Cl.
  CPC .............. *A61K 47/42* (2013.01); *A61K 47/52* (2017.08); *A61K 47/551* (2017.08); *A61K 47/64* (2017.08); *A61K 38/00* (2013.01); *C07K 2319/21* (2013.01); *C07K 2319/43* (2013.01); *C07K 2319/50* (2013.01)

(56) References Cited

OTHER PUBLICATIONS

Mowbray et al. "Conformational changes of ribose-binding protein and two related repressors are tailored to fit the functional need." J Mol Biol, 1999, 294(2).

Derosa et al., "RPtag as an Orally Bioavailable, Hyperstable Epitope Tag and Generalizable Protein Binding Scaffold," Biochemistry, 2018, pp. 3036-3049, vol. 57.

* cited by examiner

SEQUENCE LISTING

<160> NUMBER OF SEQ ID NOS: 5

<210> SEQ ID NO 1
<211> LENGTH: 253
<212> TYPE: PRT
<213> ORGANISM: Artificial Sequence
<220> FEATURE:
<223> OTHER INFORMATION: Engineered sequence

<400> SEQUENCE: 1

```
Lys Thr Ile Gly Leu Val Ile Ser Thr Leu Asn Asn Pro Phe Phe Val
1               5                   10                  15

Thr Leu Lys Asn Gly Ala Glu Glu Lys Ala Lys Glu Leu Gly Tyr Lys
            20                  25                  30

Ile Ile Val Glu Asp Ser Gln Asn Asp Ser Ser Lys Glu Leu Ser Asn
                35                  40                  45

Val Glu Asp Leu Ile Gln Gln Lys Val Asp Val Leu Leu Ile Asn Pro
50                  55                  60

Val Asp Ser Asp Ala Val Val Thr Ala Ile Lys Glu Ala Asn Ser Lys
65                  70                  75                  80

Asn Ile Pro Val Ile Thr Ile Asp Arg Ser Ala Asn Gly Gly Asp Val
                85                  90                  95

Val Ser His Ile Ala Ser Asp Asn Val Lys Gly Gly Glu Met Ala Ala
                100                 105                 110

Glu Phe Ile Ala Lys Ala Leu Lys Gly Lys Gly Asn Val Val Glu Leu
                115                 120                 125

Glu Gly Ile Pro Gly Ala Ser Ala Ala Arg Asp Arg Gly Lys Gly Phe
130                 135                 140

Asp Glu Ala Ile Ala Lys Tyr Pro Asp Ile Lys Ile Val Ala Lys Gln
145                 150                 155                 160

Ala Ala Asp Phe Asp Arg Ser Lys Gly Leu Ser Val Met Glu Asn Ile
                165                 170                 175

Leu Gln Ala Gln Pro Lys Ile Asp Ala Val Phe Ala Gln Asn Asp Glu
                180                 185                 190

Met Ala Leu Gly Ala Ile Lys Ala Ile Glu Ala Ala Asn Arg Gln Gly
                195                 200                 205

Ile Ile Val Val Gly Phe Asp Gly Thr Glu Asp Ala Leu Lys Ala Ile
                210                 215                 220

Lys Glu Gly Lys Met Ala Ala Thr Ile Ala Gln Gln Pro Ala Leu Met
225                 230                 235                 240

Gly Ser Leu Gly Val Glu Met Ala Asp Lys Tyr Leu Lys
                245                 250
```

<210> SEQ ID NO 2
<211> LENGTH: 8
<212> TYPE: PRT
<213> ORGANISM: Artificial Sequence
<220> FEATURE:
<223> OTHER INFORMATION: Engineered affinithy tag

<400> SEQUENCE: 2

```
Asp Tyr Lys Asp Asp Asp Asp Lys
1               5
```

<210> SEQ ID NO 3
<211> LENGTH: 6
<212> TYPE: PRT
<213> ORGANISM: Artificial Sequence
<220> FEATURE:
<223> OTHER INFORMATION: Engineered sequence

<400> SEQUENCE: 3

```
Glu Asn Leu Tyr Phe Gln
1               5
```

<210> SEQ ID NO 4

```
<211> LENGTH: 6
<212> TYPE: PRT
<213> ORGANISM: Artificial Sequence
<220> FEATURE:
<223> OTHER INFORMATION: Engiineered sequence

<400> SEQUENCE: 4

Glu Asn Leu Tyr Phe Ser
1               5

<210> SEQ ID NO 5
<211> LENGTH: 19
<212> TYPE: PRT
<213> ORGANISM: Artificial Sequence
<220> FEATURE:
<223> OTHER INFORMATION: Engineered sequence Nd2 P5A E18A

<400> SEQUENCE: 5

Lys Ile Ala Asn Phe Ile Pro Ala Glu Leu Lys Leu Ile Thr Lys Ala
1               5                   10                  15

Asn Val Gln
```

COMPOSITIONS, METHODS, AND SYSTEMS FOR ORALLY ADMINISTRABLE AFFINITY-BASED PROTEIN

CROSS-REFERENCE TO RELATED APPLICATIONS

This application is a U.S. national stage application of PCT/US2019/023845, filed 25 Mar. 2019, which claims benefit of priority pursuant to 35 U.S.C. § 119(e) of U.S. provisional patent application No. 62/648,170 entitled "COMPOSITIONS, METHODS, AND SYSTEMS FOR ORALLY ADMINISTRABLE AFFINITY-BASED PROTEIN," filed on 26 Mar. 2018, each of which is hereby incorporated by reference in the entirety and for all purposes.

FIELD

The disclosed compounds, compositions, processes, methods, and systems are directed to orally administered peptide-based drugs and therapies.

SEQUENCE LISTING

A sequence listing submitted in computer readable format is hereby incorporated by reference. The computer readable file is named P27464.WO01_ST25.txt was created on 24 Mar. 2019, and contains 4 kilobytes.

BACKGROUND

Therapeutic monoclonal antibodies, targeting antigens in a patient's body, have been used to treat a variety of diseases and disorders, including cancer. However, therapeutic antibodies are costly to research, discover, test, and administer. In addition, therapeutic antibodies, which are large multichain proteins prone to denaturation, cannot be used to treat targets within the patient's gut. For example, therapeutic antibodies must be maintained in physiologic conditions and administered intravenously, rather than orally, due to their size, complexity (e.g. multiple peptide chains), temperature sensitivity, stability, hydrophilicity, and susceptibility to digestion in the mammalian gastro-intestinal (GI) tract. This often requires that patients being administered therapeutic antibodies be treated in specialized treatment centers staffed by well-trained medical professionals. In some cases, treating a patient with a therapeutic antibody can cost tens or hundreds of thousands of dollars a year.

Monobodies are synthetic target-binding proteins used as an alternative to antibodies. Monobodies are similar to antibodies in that they bind targets, but are more compact and lack disulfide bonds. Monobodies have even been used as intracellular inhibitors. One monobody, based on the fibronectic type III domain (FN3) scaffold, is small (about 90 residues), stable, and easy to produce. Despite these advantages, therapeutic monobodies, because they are proteins, suffer from many of the same problems faced by antibodies.

Therapeutic proteins and peptides cannot be delivered orally without overcoming several barriers. Specifically, the gastrointestinal epithelium, enzymatic degradation by peptidases, and the harsh degradative acidic environment of the stomach act prevent oral delivery of most proteins larger than a small peptide. First, the acidic environment of the gut promotes denaturation of proteins. Second, enzymes resident throughout the gut cleave and degrade proteins and peptides into individual and short amino acid chains. Third, even if a protein manages to survive the first two barriers, the epithelium represents a formidable barrier to systemic delivery.

There is a need for inexpensive, robust, and effective protein-based drugs that can be orally delivered.

SUMMARY

The present disclosure is directed to compositions and methods for an orally administered composition useful in recognizing and binding to one or more targets within a biological system. In some embodiments, the disclosed proteins may be bi-, or tri-specific, comprising two or more targeting domains for binding two or more antigens or epitopes. In some embodiments, the compositions may be conjugated to one or more compounds for targeting to a specific cell, tissue, organ, or system. In most embodiments, the composition includes at least one protein that is stable in the GI tract, and therefore orally deliverable. In addition, the disclosed protein may be resistant to denaturation and degradation. Thus, the protein may be delivered intact to a target region within the gut, or anywhere in body to target specific molecules, cells, tissues, or organs. In several embodiments, the protein may be tagged with one or more signals, tags, or compounds that may aid in promoting absorption from the GI tract into the bloodstream.

The disclosed proteins may be modified to bind to specific target antigens. Such modifications may include mutations at or near an exposed binding site of the disclosed protein. As an example, a particular mutation may enable the protein to target a specific epitope, for example an epitope on a viral protein, or a cell surface marker or receptor, for example on a cancer cell. In various embodiments, the disclosed compound may be orally ingested as a treatment for various diseases of the gut, blood, or other tissues, systems, and organs.

In several embodiments, the disclosed composition may be a protein derived from a ribose binding protein. In these embodiments, a ribose binding protein may be truncated at or near its carboxyl end to generate a fragment known as RPtag large. In many embodiments, RPtag large may be stabilized by binding a ribose molecule and the stabilized RPtag large protein orally administered to a subject in need of treatment for a condition or disorder. In these embodiments, RPtag large may be maintained, intact, in the GI tract, or may be absorbed by a lining of the GI tract and delivered into the bloodstream intact. In one embodiment, RPtag large may be tagged with a compound, tag, or signal capable of promoting absorption of the intact PRtag large from the GI tract, and transport to the bloodstream for delivery to any cell, tissue, organ, or system in the subject.

The disclosed compositions may be useful in systemic delivery of compounds, especially proteins and peptides, via oral administration. In some embodiments, the disclosed compositions may aid in treating a disease or condition previously treated by injection (e.g. intravenous, central venous catheterization, intramuscular, subcutaneous, intraperitoneal). In many embodiments, the disclosed compositions may aid in transporting drugs, medicaments, tags, markers, etc. into the bloodstream from the gastrointestinal tract. In other embodiments, the disclosed compositions may be retained within the gastrointestinal tract to aid in treating a disease or condition in the gastrointestinal tract.

DETAILED DESCRIPTION

Disclosed herein are compositions for oral administration to a subject. In many embodiments, the disclosed compositions may include one or more proteins useful in recognizing and binding to targets within the subject's gastro-intestinal (GI) tract or outside the GI tract. In most embodiments, the disclosed protein is capable of existing in a mammalian GI tract while maintaining structural integrity. In some embodiments, the protein may be absorbed through a lining of the GI tract for systemic delivery. In many embodiments, the protein's amino acid sequence, including any mutations, binding sites, and tags may pass into the subject's bloodstream for delivery to various biological systems, organs, tissues, cells, and molecules. In many embodiments, the disclosed protein may be useful in binding to specific target antigens, as described in more detail below.

In some embodiments, a composition including a protein fragment derived from bacterial ribose binding protein is disclosed. For example, ribose binding protein may be truncated at or near its carboxyl end to generate a fragment known as RPtag large. In most embodiments, RPtag large may be a small protein, for example about 257 amino acids, and may be a single amino acid chain. Applicants have shown that RPtag large possesses excellent stability. RPtag large is resistant to many conditions and harsh environments that denature, destroy, or otherwise compromise the activity of other proteins. Applicants have also shown that RPtag large is a programmable scaffold protein that possesses the ability to recognize and bind various target antigens. In many cases, RPtag large possesses properties and characteristics similar to the much more complex, fragile, and costly mammalian antibody.

The amino acid sequence of the disclosed protein may be: KTIGLVISTLNNPFFVTLKNGAEEKAKELGYKIIVED-SQNDSSKELSNVEDLIQQKVDVLLINPVDS DAVVTAIKEANSKNIPVTIDRSANGGDVVSHI-ASDNVKGGEMAAEFIAKALKGKGNVVELEGIP GASAARDRGKGFDEAIAKYPDIKIVAKQAADFDR-SKGLSVMENILQAQPKIDAVFAQNDEMALG AIKAIEAANRQGIIVVGFDGTEDALKAIKEGKMAA-TIAQQPALMGSLGVEMADKYLK (SEQ ID NO: 1). In some embodiments, the disclosed protein may have a sequence that includes one or more mutations to the sequence above. Mutations may include one or more additions or truncations at the N- or C-terminus, one or more deletions or insertions, and one or more substitutions. Mutations may also include one or more covalently attached compounds or molecules, and/or one or more synthetic or natural amino acid branches or chains. The disclosed proteins may have more than about 55%, 60%, 65%, 70%, 75%, 80%, 85%, 90%, 94%, 95%, 96%, 97%, 98%, or 99% identity and less than about 100%, 99%, 98%, 97%, 96%, 95%, 94%, 90%, 85%, 80%, 75%, 70%, 65%, or 60% identity to SEQ ID NO:1. In many embodiments, the protein may be referred to as modified RPtag large. In some embodiments, the disclosed proteins may include two or more RPtag large proteins for targeting two or more antigens or epitopes.

RPtag large has several other desirable properties. For example, RPtag large is thermophilic (demonstrating stability and activity at a wide range of temperatures above and below physiologic temperatures), resistant to denaturants (e.g. urea, guanidine, etc.), and stable in varying pH environments (i.e. stable in both acidic, <7.0 pH and basic >7.0 pH environments). Moreover, Applicants have demonstrated RPtag large's ability to target and bind with high affinity to various antigens. In some embodiments, the disclosed composition includes a modified RPtag large, having one or more tags, signals, compounds, or mutations that may provide the RPtag large protein with additional properties or characteristics.

Modified RPtag large may be modified or tagged with one or more signals, compounds, molecules, etc. that may be useful for aiding in purification, detection, stability, cleavage, targeting, etc. As one example, a modified RPtag large may include a tag for purification, for example an N-terminal 8×His tag for purification. A modified RPtag large may include a sequence useful for detection, identification, or isolation. In some embodiments this tag may have the sequence DYKDDDDK (SEQ ID NO: 2), and may be referred to as a FLAG tag, which may be useful for detection. In another example, a modified RPtag large may include a compound or molecule for aiding in stabilization of the RPtag large structure, for example ribose. In yet another example, a modified RPtag large may include one or more sequences that may be targets for a protease, for example TEV (tobacco etch virus) protease may target a TEV sequence similar to ENLYFQ\S (SEQ ID NOs: 3/4). In some embodiments, the modified protein may include one or more mutations that may remove or add a specific residue that may be helpful for covalently modifying the protein. In one embodiment, the residue may be a cysteine (C or Cys). In some embodiments, a maleimide may be covalently attached to the protein at sulfur molecule of cysteine.

As an additional example, RPtag large may include an absorption-enhancing sequence, compound, moiety, or tag. An absorption tag may be any molecule or compound (including amino acid sequence) capable of aiding or enhancing absorption of the disclosed protein from the GI tract. An absorption tag may be covalently attached to RPtag large and facilitate its movement across the GI tract lining. In one example, RPtag large may be tagged with one or more B12 molecules to form a RPtag large-B12 construct. In some embodiments, B12 may be added via maleimide at a sulfur molecule on the protein, for example the sulfur of a cysteine residue.

Figure 4:
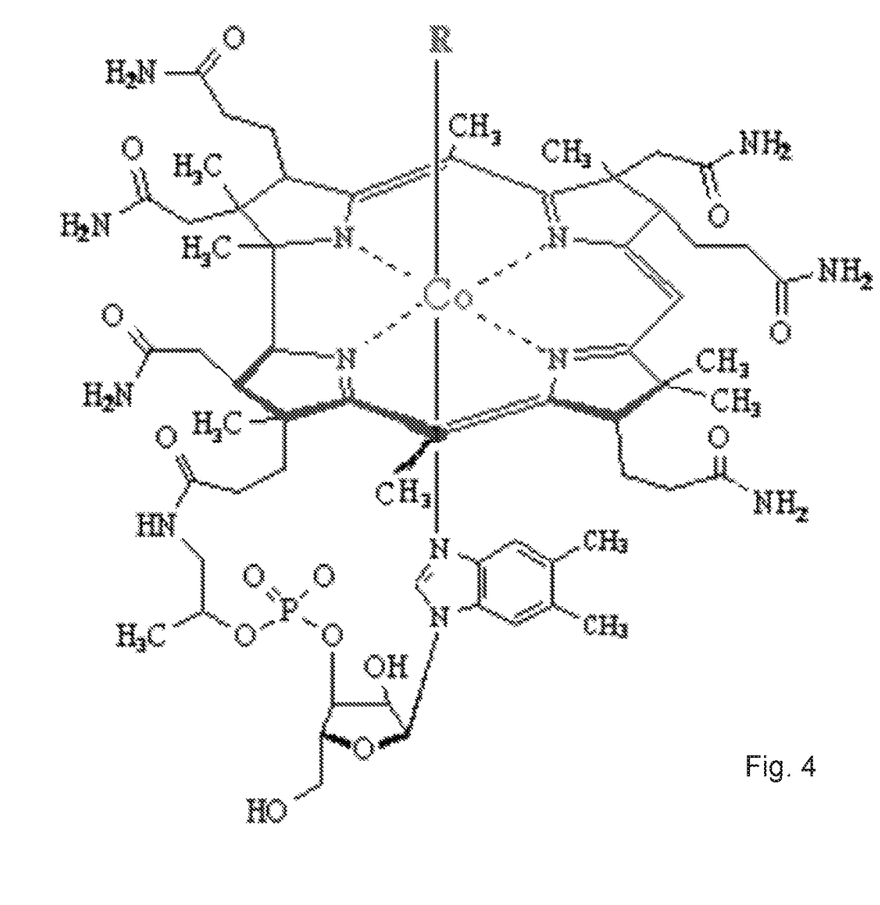
FIG. 4 shows structure of B12.

B12 (or $B_{12}$) is a vitamin with a complex chemical structure containing cobalt (see FIG. 4). B12, when orally ingested, is typically absorbed through the small intestine. Generally, if B12 enters the GI tract fused to a protein or polypeptide, it is first cleaved from the protein or polypeptide before B12 can be absorbed. Free B12 may bind to R-protein (transcobalamin-1 or haptocorrin) found in saliva and gastric fluids to protect it from degredation. The B12-R-protein complex may then pass into the small intestine. In the small intestine, B12 may be released by the R-protein and bound by the protein intrinsic factor (IF). Receptors on the surface of the ileum, the distal end of the small intestine, may absorb the IF-B12 complex. While the absorption properties of B12 make it a possible absorption tag, B12 is not known to aid in the absorption of large proteins. For example, most studies of B12 as an absorption tag involve its use with insulin, which is a small protein with a sequence of 51 amino acids and a molecular weight of about 6000 Daltons.

Figure 2:
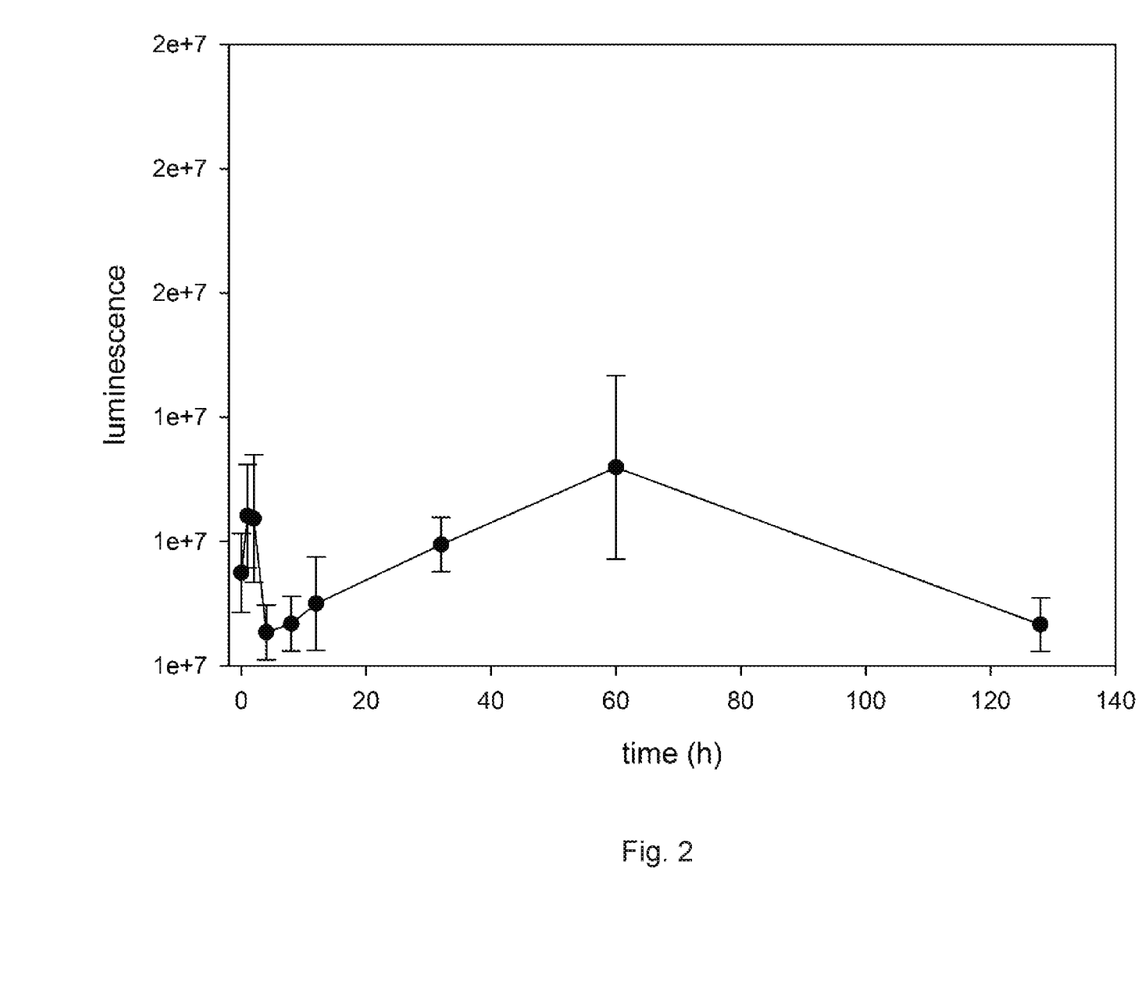
FIG. 2 is a graphical representation of serum RPtag large with cleavable absorption tag. Failed oral bioavailability trial using the reversible disulfide-linked B12. The experiment was run as for FIG. 1 and Examples, except that n=6, samples were collected over a longer duration. Raw luminescence data are presented, not concentrations. No significant difference was found using repeat-measures ANOVA. Data are mean±SEM.
Figure 3:
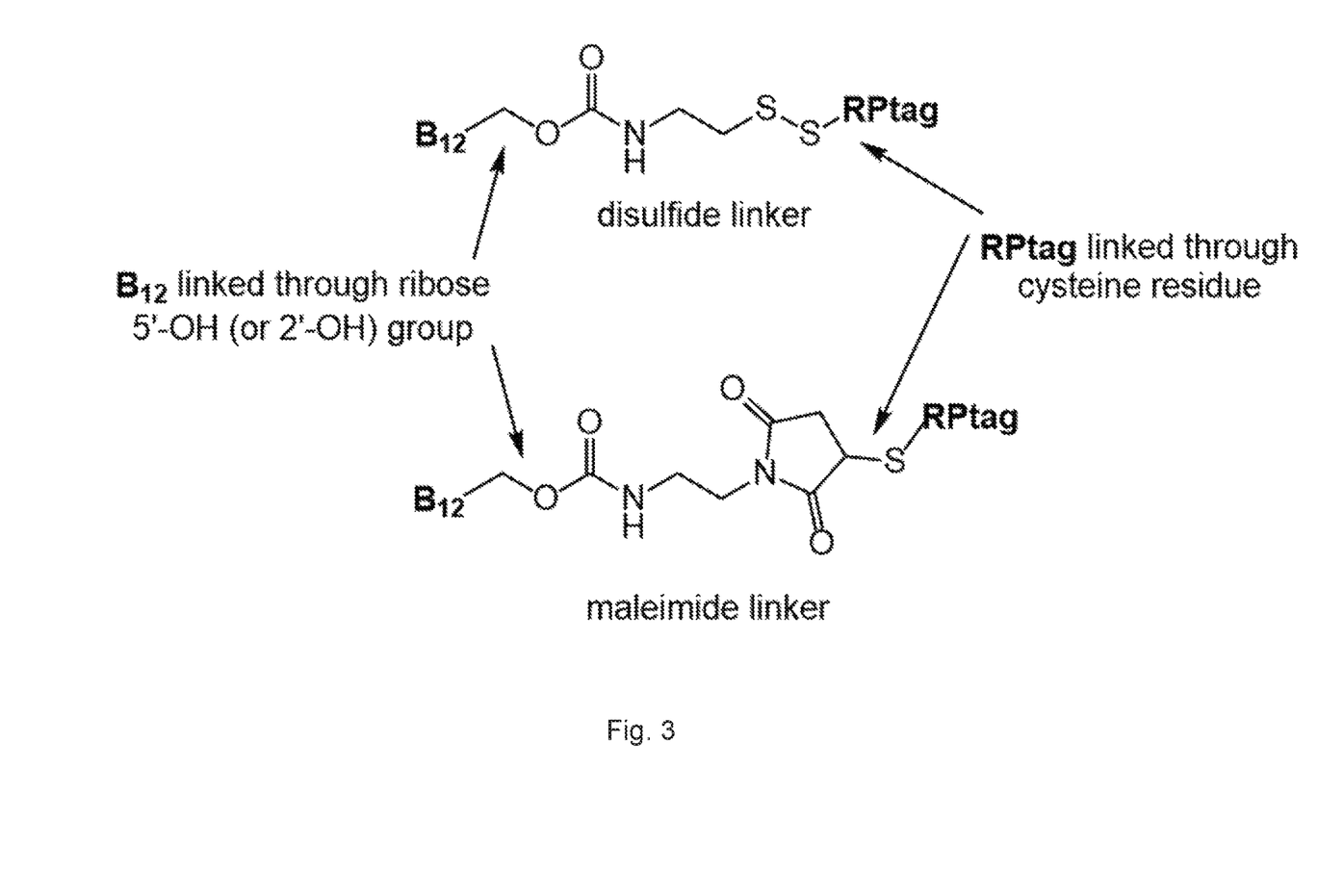
FIG. 3 shows conjugation schemes.

Surprisingly, the Applicants have discovered that a protein of greater than 250 amino acids, RPtag large conjugated to B12, may be absorbed intact from the gut, through cells lining the gut, and into the bloodstream. Applicants have demonstrated that attaching the absorption tag via a cleavable linkage, for example a disulfide bond, may result in the disclosed protein not traversing the GI endothelial layer and thus not being bio-available outside the gut. See FIG. 2.

It is contemplated that a variety of absorption tags may be useful in allowing the disclosed protein to be systemically bioavailable via oral delivery. For example, possible absorption tags may include, in addition to $B_{12}$, lectins, toxins, viral haemagglutinins, invasins, transferrin, and other vitamins capable of absorption across the lining of the GI tract (e.g., folate, riboflavin and biotin). In most embodiments, the absorption tag is not cleavable in the gut, the gut epithelium, the bloodstream, tissues, organs, or cells of a patient. In other embodiments, the absorption tag may be removed, cleaved, or modified after the disclosed protein has been absorbed from the GI tract. In these embodiments, the disclosed protein may include one or more cleavage or modification signals positioned between the RPtag large amino acid sequence and the absorption tag. In some embodiments, the cleavage or modification signal may be recognized by enzymes within the bloodstream, or may degrade over time in bloodstream. These embodiments may be referred to as prodrugs.

In another embodiment, a method of making a compound including RPtag large is disclosed. For example, RPtag large may be modified with various tags for purification, detection, stability, targeting, cleavage, etc. In one example, modified RPtag large may include one or more of a His tag, a TEV protease cleavage site, a FLAG tag, an absorption tag, or an amino acid mutation, etc.

An absorption tag may be added to the purified RPtag large protein. In one embodiment, B12 may be covalently attached to the RPtag large protein after it has been expressed. In this embodiment, the B12 may be B12-maleimide, for example, lyophilized B12-maleimide, and may be covalently attached at a cys residue on RPtag large. In other embodiments, the absorption tag may be an amino acid sequence incorporated into the disclosed protein during protein expression.

A method of orally administering a protein containing composition to a subject is described. In some embodiments, the protein is modified RPtag large. In many embodiments, the disclosed protein may be resistant to denaturation and degradation in the gastro-intestinal tract of the subject. For example, the disclosed protein may be resistant to hydrochloric acid, pepsin, salts or other molecules and conditions in the stomach. In many embodiments, the disclosed protein is stable in the stomach's pH environment, which varies between a pH of 1-3. In most embodiments, the disclosed protein may be resistant to one or more specific or non-specific enzymes within the GI tract.

The gastrointestinal tract, gut, GI tract, may refer to various structures. In some embodiments, the gastrointestinal tract may include the mouth, anus, and structures therebetween. In many embodiments, gastrointestinal structures include but are not restricted to mouth, esophagus, stomach, small intestine, cecum, large intestine/colon, appendix, and rectum The disclosed protein may be inherently stable and/or stability may be enhanced by one or more modifications. In some embodiments, the disclosed protein may be stabilized by coordinating or binding a compound or molecule, for example ribose. Ribose is a small sugar of formula $C_5H_{10}O_5$. Ribose may be a pentose (five carbon) monosaccharide (simple sugar) with linear form H—(C═O)—$(CHOH)_4$—H or six membered cyclic form (alpha- and beta-ribofuranose).

Orally administered proteins of the present disclosure may be stable in the GI tract. In many embodiments, this may allow the disclosed proteins to target cells and tissues in the GI-tract. In many embodiments, this may allow for treatment of various conditions in the GI tract, including, for example, colorectal cancer, Crohn's disease, ulcers, irritable bowel syndrome, and/or specific intestinal flora. In some embodiments, specific flora may be targeted that cause a disease or condition, for example the disclosed proteins may target *Clostridium Difficile* (*C. diff*) for the treatment of colitis. In one embodiment, RPtag large may target specific antigens in the GI tract that are involved in initiating and propagating GI tract infections and diseases, for example obesity or immune disorders. In another embodiment, modified RPtag large may be conjugated with another drug useful in treating GI tract conditions. In these embodiments, RPtag large may include one or more compounds or drugs for delivery or retention in the GI tract. As one example, RPtag large may be conjugated with one or more proton pump inhibitors (e.g., omeprazole), and help retain the inhibitor in the GI tract, and thus preventing the inhibitor from leaving the GI tract and causing systemic side effects (e.g. lysosome de-acidification, Alzheimer's disease, or kidney disease).

In another embodiment, modified RPtag large including an absorption tag is administered orally to a patient. The absorption tag may facilitate RPtag large absorption from the GI tract, thus enabling RPtag large to reach different cells, tissues, organs and organ systems outside the GI tract. This may allow for treatment of various systemic conditions. In one example, the disclosed protein may target a factor involved in a systemic disease, for example vascular endothelial growth factor (VEGF)-dependent cancers (e.g. non-small cell lung cancer and renal cell carcinoma) and/or chronic autoimmune conditions (e.g. rheumatoid arthritis and psoriasis).

In one embodiment a method of orally administering an RPtag large-B12 protein to treat a subject is disclosed. Prior to the Applicants' surprising discovery, large proteins were believed to be incapable of traversing, intact, the GI tract and entering the bloodstream. Surprisingly, Applicants have demonstrated that RPtag large-B12 may be absorbed, intact (for example greater than about 250 amino acid sequence of RPtag large), traversing the lining of the GI tract. Moreover, RPtag large was shown to be stable within and through the GI tract, and was thus identified as a full length protein (including intact binding sites at the N- and C-termini) in the bloodstream, providing a method for targeting specific biological therapeutics to sites inside, and outside the GI tract.

In one embodiment, RPtag large may be modified to bind to different target antigens prior to being orally administered. Modifications may include various mutations to the RPtag large amino acid sequence. In one embodiment, mutations may include one or more amino acid insertions, deletions, or substitutions at or near a binding cleft of the protein. In many embodiments, the binding cleft may include one or more residues between I108 and M270. In many embodiments, the mutations may be at or near I108, V120, S121, H122, I123, A124, S125, D126, K129, G130, M133, F137, L233, F237, E241, L244, I247, K248, G250, A253, A254, T255, 1256, A257, Q258, Q259, M263, L266, M270, K273, Y274, L275, or K276 (numbers correspond to sequence of SEQ ID NO:1 with an N-term leader sequence of 20-25 amino acids, for example 23). The disclosed mutations may aid in allowing the disclosed protein to bind to a target antigen with high affinity. In these embodiments, it may be useful to create specific amino acid deletions, insertions, or substitutions to help increase or decrease affinity for different target antigens. For example, a particular mutation may enable the protein to target a specific epitope, for example on a viral protein, or cell surface marker or receptor, for example, on a cancer cell. In some embodiments, as discussed above, additional amino acids may be added to the RPtag large sequence to create linker and tag sequences that may be useful in adding a label, tag, or other adduct to the protein. In these embodiments, the mutations may be located at or near the protein's C- and/or N-terminus.

Various substances may be included with formulations of the disclosed compounds and compositions. In some embodiments, the various compounds may include one or more of pharmaceutically (e.g. substance that are generally recognized as safe are well known to those of skill in the art and listed by the U.S. Food and Drug Administration) detergents, surfactants, bile salts, Ca2+ chelating agents, fatty acids, medium chain glycerides, acyl carnitine, alkanoyl cholines, N-acetylated α-amino acids, N-acetylated non-α-amino acids, chitosans, mucoadhesive polymers, and phospholipids.

EXAMPLES

Example 1—Method of Preparing RPtag Large Construct for Oral Bioavailability In one example of the present disclosure, a construct of RPtag large was formulated with sequences for an N-terminal 8×His tag for purification, an intervening TEV protease cleavage site, a 3×FLAG tag for detection, and a Cys residue to provide a —SH for site-specific labeling. This construct also included a proline residue following the 3×FLAG tag to prevent cleavage of the FLAG tag by enterokinase in the gut.

The construct was cloned into pET-28a (+); expressed in BL21 (DE3) E. coli; purified to homogeneity with a single-step NiNTA column in 50 mM Tris pH 8.0, 300 mM NaCl, 10 mM β-mercaptoethanol (β-ME) (20 mM-500 mM imidazole step gradient); dialyzed against Tris pH 8.0, 300 mM NaCl, 10 mM β-ME; and frozen at −20° C. until conjugation.

For conjugation of B12 to the expressed protein, 44 mL of frozen protein solution (~5 mg/mL) was thawed in a beaker of room temperature dH2O and pooled in a dialysis tube (12-14 kDa MWCO). The solution was exhaustively dialyzed into PBS at 4° C. (4 L volume), followed by 4 L of 50 mM NaOAc (pH 4.5)+300 mM NaCl at 4° C. overnight. Such dialysis conditions were desirable to remove β-ME and to transfer the protein into a buffer to prevent oxidation of the cysteine residue without hindering conjugation. The resulting 47.5 mL of dialysate was calculated to be 119 uM in RPtag large by A280; this equates to 188 mg of protein (4.0 mg/mL). The solution was concentrated in a spin tube (MWCO=10 kDa) to 16 mL final volume.

33 theoretical equivalents of lyophilized B12-maleimide synthesized in house was added the 16 mL of RPtag large protein in acetate buffer (pH 4.5), followed by 32 mL of 6 M guanidinium chloride buffer (pH 7.35; 150 mM sodium phosphate), which was used to rinse-in the protein solution. This calculated to a final theoretical protein concentration of 118 μM and a final guanidinium chloride concentration of 4.0 M. A stir bar was added to the tube, covered in aluminum foil, and the head space was purged with a balloon of nitrogen (to protect against possible cysteine oxidation). The solution was allowed to incubate at RT with occasional inversion by hand for 14 hours.

The B12-RPtag protein conjugate was purified away from excess B12-maleimide reagent via NiNTA chromatography. Protein was bound to the column pre-equilibrated with 6 M Gdn-HCl, 150 mM sodium phosphate, pH 7.4 and was washed with 300 mL of guanidinium chloride buffer, resulting in a clear eluent and a deep pink band of material that extended most of the length of the column. The column was washed with 100 mL of 1×PBS, followed by 250 mL of 1×PBS+20 mM imidazole, followed by 100 mL of 1×PBS. The remaining pink material was eluted with 100 mL of 500 mM EDTA solution. This removed most, but not all of the pink color by the time it began to run clear. The remaining pink material was removed with 25 mL of 6 M guanidinium chloride. The EDTA and guanidine fractions were pooled and spin concentrated (10 kDa MWCO) to remove residual guanidine and reduce the volume to 75 mL. The pink solution was flash frozen in LN2 and stored at −20° C. for approximately one week.

The flash-frozen samples were thawed in a beaker of diH2O. The samples were transferred to 2×20 cm dialysis tubes (MWCO=12-14 kDa) and rinsed-in with 2 mL of 1×PBS. The solution was dialyzed into 4 L of freshly prepared 1×PBS for 2 hours at 22° C.

The His tag was removed by incubating the protein with TEV protease to cleave the TEV sequence. For these experiments, the dialysis tubes were reopened and TEV protease was added: 10×1.4 mL tubes (0.5 mg/tube; 14 mL total) of TEV protease (produced in-house) was added to each dialysis bag (theoretical 5 mol % protease loading). The conjugate was dialyzed in the same 1×PBS solution for an additional 2 hours at 4° C. The dialysis buffer was changed (fresh 1×PBS) and dialysis was continued for an additional 2 hours at 4° C. The dialysis buffer was changed a third time (fresh 1×PBS) and dialysis was continued overnight (16 hours) at 4° C. At the end of dialysis, the solutions were bright pink and clear/homogeneous.

Post-TEV-treatment solution was spotted onto a standard stainless steel MALDI-TOF plate in a 10:1 ratio of saturated aqueous sinapinic acid solution to B12-conjugate solution. Ablation using 60% laser power yielded a clean spectrum showcasing M/1 and M/2 peaks: clean TEV-proteolysis was achieved, yielding a mixture of free RPtag large and B12-RPtag large conjugate. The crude post-TEV-treatment solution (~190 mL) was batch treated with GenScript glutathione (GSH) resin in two equal batches to remove the approximately 10 mg of residual TEV-protease (which contains a GSH fusion domain). 10 mL of GSH resin was freshly regenerated as per the manufacturer's instructions at 4° C. Approximately 2×95 mL batches were incubated with the resin on an orbital shaker at 4° C. for 1 hour. After 1 hour, the resin was allowed to settle and the solution was drained off and collected. The resulting 200 mL of solution was spin-concentrated (MWCO=10 kDa) to a final volume of 5.5 mL. The concentrated material was 0.22 um filtered and subjected to an SEC run in 1×PBS as a final polish.

Standard conditions were used for the SEC run at 2.5 h in 1×PBS with 45×2 mL fraction collection. Two major equal-area peaks were observed. These peaks may represent the monomer and dimer/aggregate of the B12-RPtag conjugate. The fractions were pooled (total volume 40.0 mL). The resulting solution was spin concentrated from 40 mL to 17.5 mL. The solution was assayed via UV-Vis absorbance and was then flash-frozen in LN2 and stored at −20° C.

The 17.5 mL of purified B12-RPtag large conjugate solution was assayed for labeling efficiency and absolute yield of B12-RPtag conjugate: 47% labeling efficiency ([B12-RPtag]=78.5 uM, [RPtag]=167 uM); 44.7 mg of B12-RPtag large conjugate in 17.5 mL (2.55 mg/mL).

Example 2—Method of Orally Administering RPtag Construct

The protein was formulated as a 2 mg/mL solution with 1 M D-ribose (to stabilize the protein) in PBS, and 500 μL of this solution was gavage fed to 12 mice (C57BL/6). To avoid competition for B12 binding proteins by dietary B12, mice were fasted for 8 hours before administration and 4 hours after administration. Serum was collected from each mouse at the indicated time points shown in FIG. 1, and assayed by ELISA.

Example 3—Assay with Capture ELISA

White Pierce™ Maleimide Activated Plates were washed 4× with 200 μL 50 mM phosphate pH 7.4, 150 mM NaCl, and reacted with 100 μL of RPtag small peptide that binds with high affinity to RPtag large. Specifically, RPtag small tight peptide (Nd2,P5A,E18A; KIANFIPAELKLIT-KANVQ; SEQ ID NO:5) with a C-terminal GGC sequence (KIANFIPAELKLITKANVQ(SEQ ID NO:5)+GGC) dissolved in 50 mM phosphate pH 7.4, 150 mM NaCl, 10 mM EDTA overnight at room temperature as bait. Plates were then washed 4× in 50 mM phosphate pH 7.4, 150 mM NaCl, and blocked for 1 hour at room temperature with 10 mM L-Cys in the same buffer, washed 4× as before, and blocked for 1 hour at room temperature with 50 mM phosphate pH 7.4, 150 mM NaCl, 1% BSA, 0.05% Tween20 (blocking buffer).

Plates were washed 4× as before, serum samples were diluted 1:100 in blocking buffer, and then serum was incubated with the baited plates for 2 hours at room temperature. On the same plate, samples of the RPtag construct of known concentration were incubated in parallel to be used as a concentration standard. These experiments captured only proteins in serum with an intact C-terminus with a binding cleft that could recognize and bind the RPtag small tight peptide affixed to the plates.

To test for intact N-termini, wells were then washed 4× as before, and incubated with a 1:10,000 dilution of HRP-conjugated mouse anti-FLAG antibody (M2 clone, 1 mg/mL stock) from Sigma-Aldrich for 1 hour at room temperature. Samples were then washed 4× as before, and assayed using SuperSignal™ ELISA Femto Substrate measured using a Molecular Devices SpectraMax i3 plate reader in luminescence mode. Low concentration standards were approximately linear and were fit with a line to estimate the concentration of RPtag large in the serum. The value at t=0 was taken before injection, and was used as a blank for the experiment.

Previous results indicated negligible binding to the plate under the tested conditions in the absence of bait peptide. Because RPtag large binds the bait peptide at the C-terminus, and the 3×FLAG peptide recognized by the detection antibody is at the N-terminus, this assay reported only on full-length RPtag large that retained its binding activity, as any truncation would remove either the N- or C-terminal binding epitopes necessary for detection in this assay, and a lack of binding activity would eliminate binding to the bait peptide immobilized on the plate.

Figure 1:
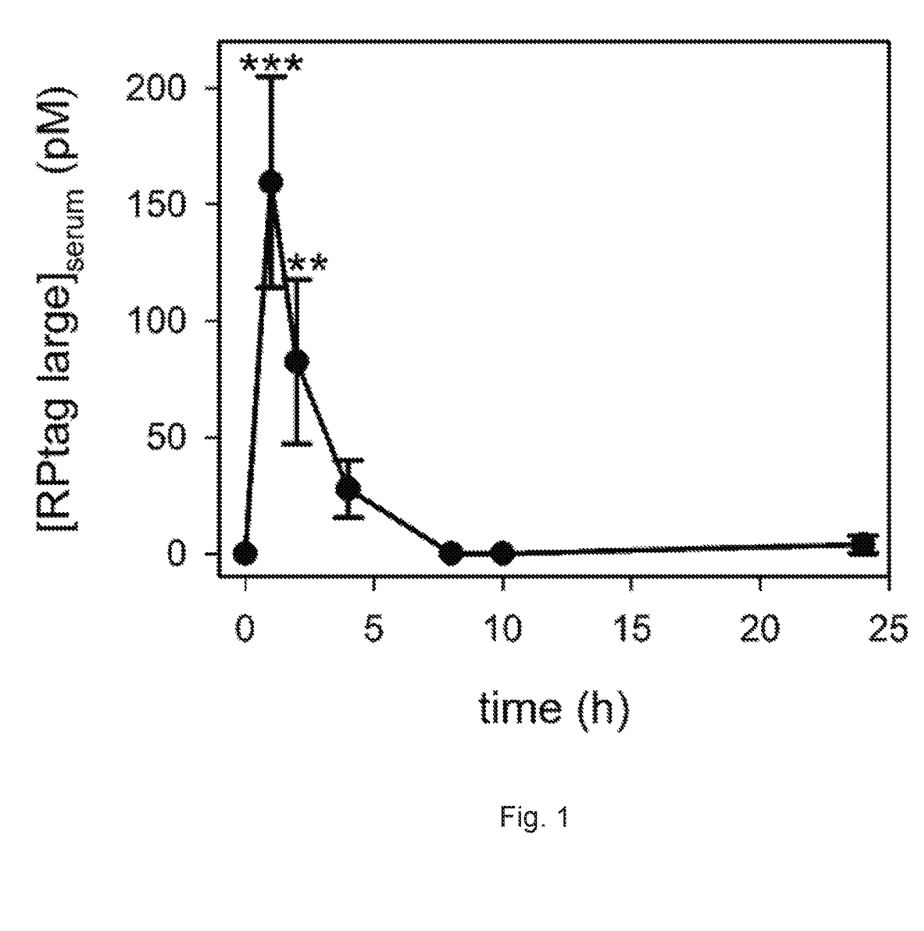
FIG. 1 is a graphical representation of oral bioavailability of RPtag large conjugated to non-cleavable absorption tag.

FIG. 1 is a graphical representation of one embodiment of oral bioavailability of RPtag large over time, specifically showing the results of the assay. In the figure, data are mean±SE. The data were analyzed by repeat measures ANOVA on ranks with Dunn's post-hoc correction relative to t=0. *$p<0.001$, $p<0.01$. FIG. 1 shows at least two properties of RPtag large: its stability in the GI tract and its compatibility with absorption tags. In the example depicted in FIG. 1, a RPtag large-B12 construct that is orally administered may be rapidly absorbed through a GI tract and into another biological system, in this case, into a serum. The plot points on the graph show the presence of full-length RPtag large in the serum. In this example, the construct was eliminated with a half-life within hours. The normal range for serum B12 tops out at ~670 pM, suggesting the experiment was within a range that the system is capable of handling.

Other methods are described in the text or in the figure legends.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. For example, the experiments presented herein should not be construed to limit the changes that can be introduced into RPtag(large) to alter its binding affinity, specificity, stability, or ability to interact with one or more drugs, compounds, substance, or molecules, including, but not limited to therapeutic compounds and medicaments. Accordingly, the detailed description is to be regarded as illustrative in nature and not restrictive.

All references disclosed herein, whether patent or non-patent, are hereby incorporated by reference as if each was included at its citation, in its entirety. In case of conflict between reference and specification, the present specification, including definitions, will control.

Although the present disclosure has been described with a certain degree of particularity, it is understood the disclosure has been made by way of example, and changes in detail or structure may be made without departing from the spirit of the disclosure as defined in the appended claims.

We claim:

1. A composition for oral administration comprising:
   a protein comprising an amino acid sequence with greater than about 80% identity to RPtag large (SEQ ID NO:1); and
   a ribose molecule.

2. The composition of claim 1, further comprising an absorption tag for absorption from a lining in a gastrointestinal tract.

3. The composition of claim 2, wherein the absorption tag is B12.

4. The composition of claim 3, further comprising a bicarbonate.

5. The composition of claim 3, wherein the protein is modified for targeting one or more antigens.

6. The composition of claim 5, wherein the modification is at least one of an addition, deletion or substitution of one or more amino acids in SEQ ID NO:1.

7. The composition of claim 3, further comprising a drug useful in treating gastrointestinal tract conditions.

8. The composition of claim 1, further including at least one pharmaceutically acceptable substance.

9. A method of making a modified protein for oral administration comprising:
   creating a first coding sequence for a first amino acid sequence of a protein, the first amino acid sequence comprising an amino acid sequence with greater than about 80% identity to the protein sequence of RPtag large (SEQ ID NO:1);
   adding one or more second coding sequences to the first coding sequence, wherein the one or more second coding sequences code for amino acid sequences useful for at least one of purification, detection, and cleavage; and
   expressing the first and second coding sequences to create the modified protein, and adding an absorption tag to the modified protein for absorption from a lining in a gastrointestinal tract.

10. The method of claim 9, wherein the first amino acid sequence includes at least one of an addition, deletion or substitution of one or more amino acids in SEO ID NO:1.

11. The method of claim 9, wherein the one or more second coding sequences code for at least one of a His tag for purification, a FLAG tag for detection, and a TEV sequence for cleavage.

12. The method of claim 9, further including the step of binding a bicarbonate to the modified protein.

13. The method of claim 9, wherein the absorption tag is B12.

14. The method of claim 9, further comprising binding a drug useful in treating gastrointestinal tract conditions to the modified protein.

15. A method of treating a gastrointestinal tract disease or condition by orally administering a modified protein comprising:
   providing
      a protein comprising an amino acid sequence with greater than about 80% identity to RPtag large (SEQ ID NO:1); and
      a ribose molecule to create a drug composition; and
   administering an effective amount of the drug composition to a patient via oral delivery, wherein the patient is in need of treatment for a gastrointestinal tract disease or condition.

16. The method of claim 15, wherein the gastrointestinal tract disease or condition is selected from colorectal cancer, Crohn's disease, an ulcer, irritable bowel syndrome, and *Clostridium difficile* colitis.

17. The method of claim 15, wherein the drug composition further includes a drug compound useful in treating the gastrointestinal tract disease or condition.

18. A method of treating a systemic condition in a subject with a modified protein comprising:
   providing a drug composition comprising
      a protein comprising an amino acid sequence with greater than about 80% identity to RPtag large (SEQ ID NO:1);
      a ribose molecule; and
      an absorption tag for absorption from a lining in a gastrointestinal tract; and
   administering an effective amount of the drug composition to a patient in need of treatment for a systemic condition.

19. The method of claim 18, wherein the absorption tag is B12 covalently attached to the protein.

\* \* \* \* \*

UNITED STATES PATENT AND TRADEMARK OFFICE
CERTIFICATE OF CORRECTION

| | | |
|---|---|---|
| PATENT NO. | : 11,407,791 B2 | |
| APPLICATION NO. | : 17/041780 | |
| DATED | : August 9, 2022 | |
| INVENTOR(S) | : Adam Blanden and Aaron Wolfe | |

It is certified that error appears in the above-identified patent and that said Letters Patent is hereby corrected as shown below:

In the Claims

Column 13, Line 67 (Claim 10, Line 3) reads:
"amino acids in SEO ID NO: 1."
Should be:
--amino acids in SEQ ID NO: 1.--

Signed and Sealed this
Twentieth Day of June, 2023

*Katherine Kelly Vidal*

Katherine Kelly Vidal
*Director of the United States Patent and Trademark Office*